United States Patent [19]
Shervington et al.

[11] Patent Number: 6,047,865
[45] Date of Patent: Apr. 11, 2000

[54] GAS CAPSULE AND GAS DELIVERY SYSTEM

[75] Inventors: Evelyn A. Shervington, Nr. Petersfield; David W. Birch, Bordon; David Surman, Guildford, all of United Kingdom

[73] Assignee: The BOC Group plc, Windlesham, United Kingdom

[21] Appl. No.: 08/899,522

[22] Filed: Jul. 24, 1997

[30] Foreign Application Priority Data

Jul. 24, 1996 [GB] United Kingdom .................. 96 15589
Apr. 24, 1997 [GB] United Kingdom .................. 97 08260

[51] Int. Cl.[7] .................................................. B65D 47/10
[52] U.S. Cl. ................................... 222/541.1; 222/541.6; 222/637; 604/70; 604/200
[58] Field of Search ............................... 222/637, 321.6, 222/541.1, 541.6; 604/216, 68, 70, 200, 148

[56] References Cited

U.S. PATENT DOCUMENTS

| 3,892,237 | 7/1975 | Steiner | 604/216 |
| 5,288,159 | 2/1994 | Wirt | 222/541.6 |
| 5,531,707 | 7/1996 | Kers et al. | 222/541.6 |
| 5,899,880 | 5/1999 | Bellhouse et al. | 604/70 |

FOREIGN PATENT DOCUMENTS 253744  8/1925  United Kingdom .

*Primary Examiner*—Philippe Derakshani
*Attorney, Agent, or Firm*—Philip H. Von Neida; Salvatore P. Pace

[57] ABSTRACT

A capsule for storing a fluid, for example helium, under pressure comprises a hollow body from which extends a hollow neck. A stopper engages with the neck in a fluid tight manner. The stopper includes a main hollow portion and a stem extending outwardly from the main hollow portion. The root of the stem where it joins the main hollow portion forms a frangible section which, when broken, will allow fluid in the capsule to escape under pressure.

4 Claims, 2 Drawing Sheets

GAS CAPSULE AND GAS DELIVERY SYSTEM

The present invention relates to gas delivery systems and in particular to capsules for containing small volumes of fluid at high pressure, that is, between 60 and 80 bar for use in such systems.

BACKGROUND OF THE INVENTION

Sealed capsules are well known in circumstances where the force of the fluid under pressure is employed to dispense a substance such as discharging draught beer from a beer dispenser or expelling soda water from a soda siphon.

It is also known to employ sealed capsules containing helium at high pressures in the order of 30–40 bar in medical devices using the energy of the pressurized helium to drive a therapeutic agent through the skin of a patient.

In PCT published application WO94/24263, there is described a needle-less syringe, which includes a metal capsule containing helium gas at high pressure which is used to force particles of a therapeutic agent through the skin of a patient in a substantially painless manner. The capsule is detachable from the remainder of the syringe and once used, either a new charge of gas can be placed in the capsule, or more favorably, the capsule can be discarded and a new capsule charged with gas attached to the remainder of the syringe.

In the circumstance where the gas capsule is a throw away item, it is important that it can be manufactured simply and cheaply. In medical applications, helium gas is a favored fluid since it is very light which makes it suitable for use as a propellant for therapeutic agents in that when it impinges against the skin of a patient, it will bounce off into the atmosphere and not pass through. However, because helium is light, it is difficult to contain since it will leak through the most minuscule fault in a container. Further, in medical applications it is important that the helium gas can be released from the gas capsule with the minimum of force by the user, for example, finger force.

UK Patent 253744 describes a metal capsule for gases or liquids under pressure which can be used to inflate a flexible container. The capsule comprises a cylindrical hollow body having a neck portion formed with an internal thread. A closure member has a corresponding external thread and is screwed into the neck portion.

The closure member has an outwardly projecting stem which is hollowed so that it may easily be broken. The stem has an external thread for connection to a handle forming part of the flexible container. When it is required to liberate the gases or liquids in the capsule, the hollow body is moved laterally relative to the handle and the stem connected thereto such that the stem is ruptured thereby releasing the gas from the interior of the hollow body.

The capsule described in UK Patent 253744 is not effective for retaining a very light gas such as helium for a reasonable length of time at pressures in the order of 60 to 80 bar since the helium molecules will leak through the helical path between the co-operating internal thread of the neck portion and external thread on the closure member. Further, in order to break the stem, a considerable lateral force needs to be applied, that is, a force greater than finger pressure having no mechanical advantage. A further disadvantage is that the capsule is expensive to manufacture in that screw threads have to be turned on both the neck portion and the closure member.

In accordance with the present invention, there is provided a gas delivery system including a capsule for fluid under high pressure which can be manufactured simply and cheaply. The capsules of the invention are suitable for retaining, substantially leak-proof, a fluid under pressure, for example, helium gas.

Finally, the capsules of the present invention are advantageous in that they can be opened with a finger pressure having no or relatively very little mechanical advantage without causing the gas delivery device of which it forms a part, to move when held in one hand.

SUMMARY OF THE INVENTION

There is provided in accordance with the present invention, a gas delivery system including capsule for storing a fluid under pressure which comprises a hollow body with a neck extending therefrom and a stopper, the stopper and the neck fitting together in a fluid tight manner, the stopper comprising a main hollow portion and the stem extending outwardly from the main hollow portion, the root of the stem where it joins the main hollow portion forming a frangible section which, when broken, will allow the fluid under pressure to escape from the capsule.

DETAILED DESCRIPTION OF THE INVENTION

In accordance with the present invention, a gas delivery system comprises a casing formed with an outlet and containing a capsule, preferably of aluminium or an aluminium alloy, for storing a fluid under pressure, the capsule having a hollow body with a neck extending therefrom and a stopper, the stopper and the neck fitting together in a fluid tight manner, the stopper comprising a main hollow portion and a stem extending outwardly from the main hollow portion. The root of the stem where it joins the main hollow portion of the capsule forms a frangible section. The system casing has mechanical means arranged within for rupturing the frangible section thereby allowing the escape of the fluid from the capsule which thereafter exits through the outlet of the casing.

Preferably the mechanical means includes an inclined surface for engaging and thereby exerting a lateral force on the stem for rupturing the frangible section.

Figure 1:
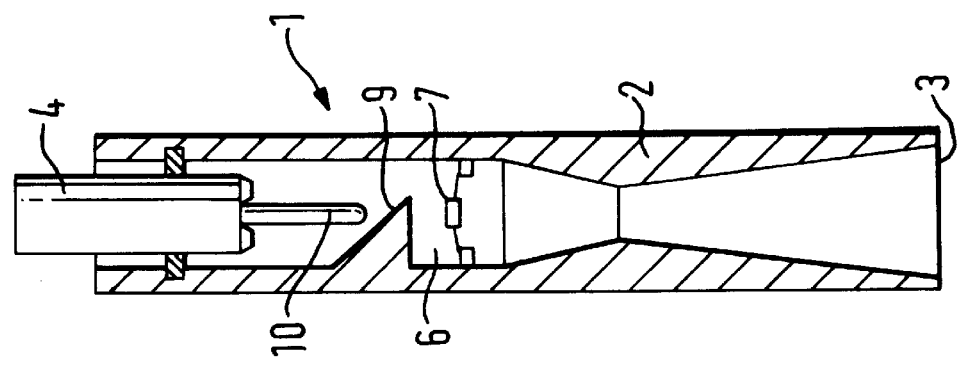
FIG. 1 is a diagrammatic sketch of a needle-less medical device including a gas delivery system of the present invention.

As shown in FIG. 1, a needle-less medical device is in the form of a needle-less syringe 1 which comprises essentially a casing 2 in the form of an elongate hollow tube open at a distal end to define an outlet 3. The casing 2 contains a gas capsule 4 having a hollow body for storing a fluid, for example, helium under high pressure, that is between 60 and 80 bar. An inclined surface 9 is formed on the interior of the surface of the casing 2 spaced from but adjacent to a solid stem 10 extending from a stopper 5 shown in detail in FIG. 2 of the gas capsule 4. The gas capsule 4 is so mounted within the casing 2 that when a finger pressure is applied to the proximal end of the gas capsule 4 the capsule will move downwardly (as shown) until the stem 10 of the stopper 5 shown in detail in FIG. 2 strikes the surface 9. Within the casing 2 adjacent the stem 10 of the stopper 5 shown in detail in FIG. 2 there is formed a chamber 6 for receiving a powdered agent, for example, a drug 7.

Figure 2:
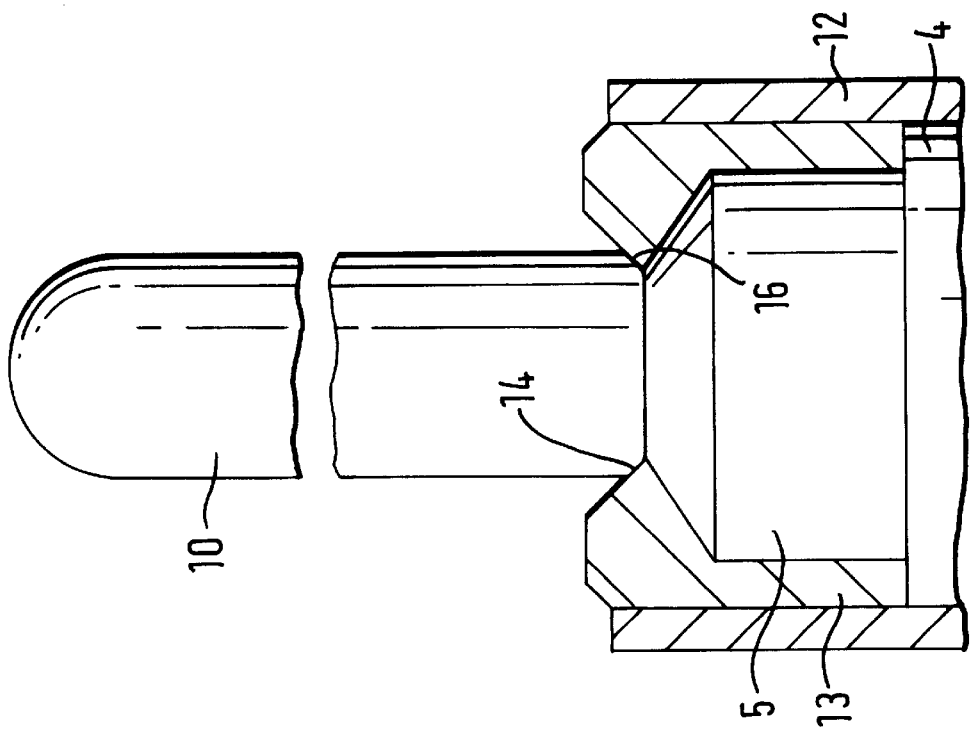
FIG. 2 is a side view of a hollow neck together with a stopper of a capsule for storing a fluid under pressure.

Referring also to FIG. 2, the stopper 5 which is laser welded within a hollow neck 12 of the gas capsule 4 includes a main hollow body part 13 from which extends the stem 10. The main hollow portion of the stopper may be located either within the neck or over the neck in a fluid-tight manner. The root 14 of the stem 10 where it is joined to the main hollow body 13 forms a frangible section 16. The stem 10 may be either solid or hollow. It will be apparent that the interior of the main hollow body 13 is in communication with the hollow interior of the gas capsule 4.

In use, when it is desired to treat a patient by means of the syringe 1, the drug 7 is placed in the chamber 6 and the outlet 3 is placed against the skin of the patient Finger pressure is applied to the proximal (upper as shown) end of the gas capsule 4 which causes the capsule 4 to move downwardly until the stem 10 of the stopper 5 engages the inclined surface 9 thereby rupturing about the frangible section 16 with the subsequent release of helium. The released helium passes out from the capsule 4 into the chamber 6 where it entrains the powdered drug 7. The helium with the entrained powdered drug 7 then passes through the outlet 3 with the drug passing through the skin of the patient while the light molecules of helium bounce off the skin into the atmosphere.

Figure 3:
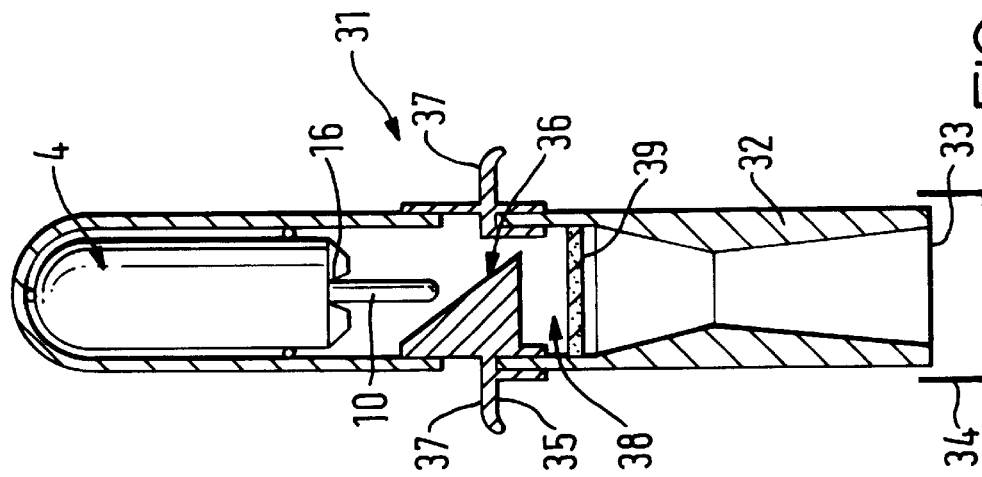
FIG. 3 is a diagrammatic sketch of a further needle-less medical device including a gas delivery system of the present invention.

Referring now to FIG. 3, a needle-less medical device in the form of a needle-less syringe 31 comprises essentially a casing 32 in the form of an elongated hollow tube open (when in use) at a distal end to define an outlet 33 but prior to use covered by a cap 34. The opposite proximal (upper as shown) end, is sealed. As with the embodiment illustrated in FIG. 1 the casing 32 contains a gas capsule 4 located adjacent the sealed proximal end of the casing. The gas capsule 4 has a hollow body for storing a fluid, for example helium, under high pressure, that is, between 60 and 80 bar, and a stopper 5 which includes a solid stem 10 extending outwardly (downwardly) as shown from the stopper 5 of the gas capsule 4.

An actuator member 35 is mounted for sliding movement on the casing 32 which includes an inclined surface 36 located adjacent the free end of the stem 10. The member 35 also includes two wings 37 extending outwardly from the casing 32. Within the casing 32 adjacent the free end of the stem 10 there is formed a chamber 38 for receiving a powdered drug mounted on a membrane 39.

In use, when it is desired to treat a patient by means of the syringe 31, the powdered drug is placed on the membrane 39 within the chamber 38, the cap 34 is removed and the outlet 33 is placed against the skin. Finger pressure is applied to the wings 37 to slide the actuator member 35 upwardly (as shown) relative to the casing 32 thereby causing the inclined surface 36 to engage and apply a lateral force to the stem 10. This will cause the stem 10 to rupture about the frangible section 16 with the subsequent release of helium. As with the embodiment illustrated in FIG. 1, the helium with the entrained powdered drug will burst the membrane 39 and pass through the outlet 33 with the drug passing through the skin of the patient while the light helium molecules bounce off the skin into the atmosphere.

An advantage of the embodiment illustrated in FIG. 3 is that, since the upper (as shown) end of the casing 32 is sealed, the gas capsule 4 will be held in place when the stem 10 is ruptured so that it does not fly out from the casing 32 due to the reaction force of the escaping helium.

The hollow body of the gas capsule 4 together with the stopper 5 may be made from aluminium or aluminium alloy and, if necessary, the body of the capsule may be reinforced with an outer layer of a different material which could be in the form of a lattice wound tightly around a substantial part of the hollow body.

It will be appreciated that the capsule 4 described is relatively easy to manufacture and the design of the stopper 5 is such that when the frangible section 16 is ruptured it will leave a relatively large orifice through which the helium can escape.

Figure 4:
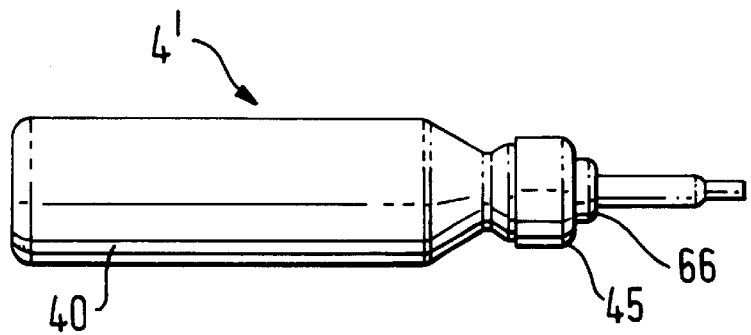
FIG. 4 is a plan view of a second embodiment of a capsule for storing a fluid under pressure.
Figure 5:
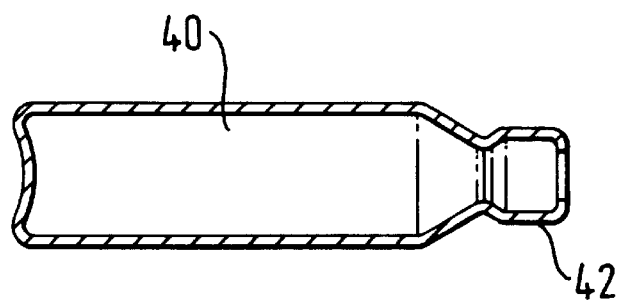
FIG. 5 is a cross-section through a hollow body forming part of the capsule of FIG. 4.
Figure 6:
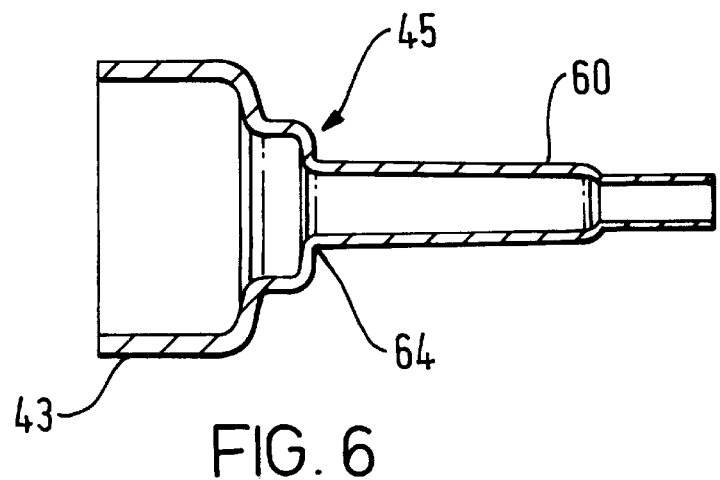
FIG. 6 is a cross-section through a stopper forming part of the capsule of FIG. 4.

Referring now to FIGS. 4, 5 and 6, a second embodiment of gas capsule 4' is illustrated which includes a hollow body 40 for storing a fluid, for example helium, under high pressure, that is between 60 and 80 bar. As illustrated best in FIG. 5 the hollow body 40 terminates at one end in a hollow neck 42. A stopper 45, best illustrated in FIG. 6, includes a main hollow portion 43 from which extends a hollow stem 60. The root 64 of the stem 60 where it is joined to the main hollow portion 43 forms a frangible section 66 shown in FIG. 4. As shown in FIG. 4, the main hollow portion 43 of the stopper 45 is fitted over the hollow neck 42 and laser welded to form a fluid tight joint. The hollow body 40 of the gas capsule 4' together with the stopper 45 may be made from aluminium or an alloy of aluminium. It will be apparent that the capsule 4' is intended to be used with the needleless syringes 1 and 31 in the same manner as gas capsule 4.

Although reference has been made to the use of the capsules 4, 4' with a needle-less syringe for medical purposes, there are a number of other applications where the force of the contained fluid can be utilized. For example, in the inflation of balloons bearing fluorescent markings for identification by radar and for the inflation of life jacket dinghies. The energy of the pressurized fluid could also be utilized in a weapon to act as a propellant for a bullet or other projectile. Further, the force of the fluid under pressure can be employed to dispense a substance such as discharging draft beer from a beer dispenser, or expelling soda water from a soda siphon.

We claim:

1. A capsule for storing a fluid under pressure, comprising a hollow body with a neck extending therefrom and a stopper, the stopper and the neck fitting together in a fluid tight manner, the stopper comprising a main hollow portion located within the neck in a fluid tight manner and in fluid communication with the interior of said hollow body and the solid stem extending outwardly from the main hollow portion, the root of the stem where it joins the main hollow portion forming a frangible section which, when broken, will allow fluid under pressure contained therein to escape from the capsule.

2. A capsule in accordance with claim 1, wherein the main hollow portion of the stopper is located over the neck in a fluid tight manner.

3. A capsule in accordance with claim 2, wherein the stem is hollow.

4. A capsule in accordance with claim 1, wherein the capsule is made of aluminium or an aluminium alloy.

* * * * *